United States Patent
Shalev et al.

(10) Patent No.: US 9,526,638 B2
(45) Date of Patent: Dec. 27, 2016

(54) IMPLANTABLE MEDICAL DEVICES CONSTRUCTED OF SHAPE MEMORY MATERIAL

(75) Inventors: Alon Shalev, Ra'anana (IL); Raphael Benary, Tel Aviv (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 0 days.

(21) Appl. No.: 13/807,880

(22) PCT Filed: Feb. 2, 2012

(86) PCT No.: PCT/IL2012/000060
§ 371 (c)(1),
(2), (4) Date: Feb. 8, 2013

(87) PCT Pub. No.: WO2012/104842
PCT Pub. Date: Aug. 9, 2012

(65) Prior Publication Data
US 2013/0131783 A1 May 23, 2013

Related U.S. Application Data

(60) Provisional application No. 61/438,977, filed on Feb. 3, 2011.

(51) Int. Cl.
*A61F 2/82* (2013.01)
*A61F 2/95* (2013.01)
(Continued)

(52) U.S. Cl.
CPC . *A61F 2/82* (2013.01); *A61F 2/95* (2013.01); *A61F 2/97* (2013.01); *A61F 2/07* (2013.01); *A61F 2002/9511* (2013.01)

(58) Field of Classification Search
CPC ............... A61F 2002/9511; A61F 2/95
(Continued)

(56) References Cited

U.S. PATENT DOCUMENTS

| | | | |
|---|---|---|---|
| 4,355,426 A | 10/1982 | MacGregor |
| 4,505,767 A | 3/1985 | Quin |

(Continued)

FOREIGN PATENT DOCUMENTS

| | | |
|---|---|---|
| CA | 2 497 704 | 3/2004 |
| CN | 101045022 | 10/2007 |

(Continued)

OTHER PUBLICATIONS

"E-vita® open plus" product brochure (JOTEC GmbH, Hechingen, Germany) (2010).

(Continued)

*Primary Examiner* — Brian Pellegrino
(74) *Attorney, Agent, or Firm* — Sughrue Mion, PLLC

(57) ABSTRACT

Medical apparatus (100) is provided for insertion into a mammalian body. The apparatus (100) includes structural stent elements (110), at least a portion of which are shaped so as to define (a) at least one generally circumferential band (112), and (b) a plurality of engagement members (114) that are joined to and extend radially inwardly from the band (112). The apparatus (100) further includes an elongated latch member (118) which is threaded through the engagement members (114), thereby physically latching the engagement members (114). The band (112) and the engagement members (114) are configured such that (a) when the latch member (118) is threaded through and thus physically latches the engagement members (114), the engagement members (114) retain the band (112) in a radially-compressed state, and (b) when the latch member (118) is removed from the engagement members (114), the band (112) assumes a radially-expanded state. Other embodiments are also described.

5 Claims, 8 Drawing Sheets

(51) Int. Cl.
*A61F 2/97* (2013.01)
*A61F 2/07* (2013.01)

(58) Field of Classification Search
USPC .......................... 623/1.12, 1.15, 1.11, 1.13
See application file for complete search history.

(56) References Cited

U.S. PATENT DOCUMENTS

| | | |
|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,192,286 A | 3/1993 | Phan et al. |
| 5,234,448 A | 8/1993 | Wholey et al. |
| 5,425,739 A | 6/1995 | Jessen |
| 5,439,446 A | 8/1995 | Barry |
| 5,456,694 A * | 10/1995 | Marin et al. ................. 623/1.11 |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,575,818 A | 11/1996 | Pinchuk |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,774 A | 5/1998 | Pinchuk |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,792,172 A | 8/1998 | Fischell et al. |
| 5,824,040 A | 10/1998 | Cox et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,944,750 A | 8/1999 | Tanner et al. |
| 5,976,178 A | 11/1999 | Goldsteen et al. |
| 5,980,552 A | 11/1999 | Pinchasik et al. |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,059,824 A | 5/2000 | Taheri |
| 6,077,298 A | 6/2000 | Tu |
| 6,099,497 A | 8/2000 | Adams et al. |
| 6,117,145 A | 9/2000 | Wood et al. |
| 6,156,064 A | 12/2000 | Chouinard |
| 6,168,615 B1 | 1/2001 | Ken |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,312,458 B1 | 11/2001 | Golds |
| 6,319,287 B1 | 11/2001 | Frimberger |
| 6,325,823 B1 | 12/2001 | Horzewski et al. |
| 6,344,056 B1 | 2/2002 | Dehdashtian |
| 6,428,565 B1 | 8/2002 | Wisselink |
| 6,451,048 B1 | 9/2002 | Berg et al. |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,565,597 B1 | 5/2003 | Fearnot et al. |
| 6,613,075 B1 | 9/2003 | Healy et al. |
| 6,613,078 B1 | 9/2003 | Barone |
| 6,635,083 B1 | 10/2003 | Cheng et al. |
| 6,648,901 B2 | 11/2003 | Fleischman et al. |
| 6,652,567 B1 | 11/2003 | Deaton |
| 6,652,571 B1 | 11/2003 | White et al. |
| 6,656,214 B1 | 12/2003 | Fogarty et al. |
| 6,692,520 B1 | 2/2004 | Gambale et al. |
| 6,695,833 B1 | 2/2004 | Frantzen |
| 6,695,875 B2 | 2/2004 | Stelter et al. |
| 6,730,117 B1 | 5/2004 | Tseng et al. |
| 6,743,195 B2 | 6/2004 | Zucker |
| 6,748,953 B2 | 6/2004 | Sherry et al. |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,198,638 B2 | 4/2007 | Dong |
| 7,201,772 B2 | 4/2007 | Schwammenthal et al. |
| 7,223,266 B2 | 5/2007 | Lindenbaum et al. |
| 7,261,733 B1 | 8/2007 | Brown |
| 7,279,003 B2 | 10/2007 | Berra et al. |
| 7,294,145 B2 | 11/2007 | Ward |
| 7,306,623 B2 | 12/2007 | Watson |
| 7,341,598 B2 | 3/2008 | Davidson et al. |
| 7,393,357 B2 | 7/2008 | Stelter et al. |
| 7,399,313 B2 | 7/2008 | Brown |
| 7,407,509 B2 | 8/2008 | Greenberg et al. |
| 7,413,573 B2 | 8/2008 | Hartley et al. |
| 7,429,269 B2 | 9/2008 | Schwammenthal |
| 7,442,204 B2 | 10/2008 | Schwammenthal |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,616,997 B2 | 11/2009 | Kieval |
| 7,637,939 B2 | 12/2009 | Tischler |
| 7,662,161 B2 | 2/2010 | Briganti et al. |
| 7,662,168 B2 | 2/2010 | McGuckin, Jr. et al. |

(56) References Cited

U.S. PATENT DOCUMENTS

| | | |
|---|---|---|
| 7,678,141 B2 | 3/2010 | Greenan et al. |
| 7,722,626 B2 | 5/2010 | Middleman et al. |
| 7,731,732 B2 | 6/2010 | Ken |
| 7,803,178 B2 | 9/2010 | Whirley et al. |
| 7,815,673 B2 | 10/2010 | Bloom et al. |
| 7,887,575 B2 | 2/2011 | Kujawski |
| 7,955,373 B2 | 6/2011 | Sowinski et al. |
| 7,959,662 B2 | 6/2011 | Erbel et al. |
| 7,998,186 B2 | 8/2011 | Hartley |
| 8,016,853 B2 | 9/2011 | Griffen et al. |
| 8,021,419 B2 | 9/2011 | Hartley et al. |
| 8,048,147 B2 | 11/2011 | Adams |
| 8,052,741 B2 | 11/2011 | Bruszewski et al. |
| 8,066,755 B2 | 11/2011 | Zacharias et al. |
| 8,080,026 B2 | 12/2011 | Konstantino |
| 8,080,053 B2 | 12/2011 | Satasiya et al. |
| 8,133,267 B2 | 3/2012 | Leonhardt et al. |
| 8,157,852 B2 | 4/2012 | Bloom et al. |
| 8,167,926 B2 | 5/2012 | Hartley et al. |
| 8,172,892 B2 | 5/2012 | Chuter et al. |
| 8,172,895 B2 | 5/2012 | Anderson et al. |
| 8,226,706 B2 | 7/2012 | Hartley et al. |
| 8,236,040 B2 | 8/2012 | Mayberry et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,470,018 B2 | 6/2013 | Hartley et al. |
| 8,491,646 B2 | 7/2013 | Schreck |
| 2001/0000188 A1 | 4/2001 | Lenker et al. |
| 2001/0004705 A1 | 6/2001 | Killion et al. |
| 2001/0010006 A1 | 7/2001 | Bachinski et al. |
| 2001/0014823 A1 | 8/2001 | Resseman et al. |
| 2001/0034550 A1 | 10/2001 | Buirge et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0111667 A1* | 8/2002 | Girton et al. ............ 623/1.13 |
| 2002/0123791 A1 | 9/2002 | Harrison |
| 2002/0156495 A1 | 10/2002 | Brenneman et al. |
| 2002/0173809 A1 | 11/2002 | Fleischman et al. |
| 2002/0183783 A1 | 12/2002 | Shadduck |
| 2002/0193864 A1 | 12/2002 | Khosravi et al. |
| 2003/0040791 A1 | 2/2003 | Oktay |
| 2003/0057156 A1 | 3/2003 | Peterson et al. |
| 2003/0074055 A1 | 4/2003 | Haverkost |
| 2003/0093145 A1 | 5/2003 | Lawrence-Brown et al. |
| 2003/0130720 A1 | 7/2003 | DePalma et al. |
| 2003/0144725 A1 | 7/2003 | Lombardi |
| 2003/0153968 A1 | 8/2003 | Geis et al. |
| 2003/0163187 A1 | 8/2003 | Weber |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0208192 A1 | 11/2003 | Truckai et al. |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0162606 A1 | 8/2004 | Thompson |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215320 A1 | 10/2004 | MacHek |
| 2004/0215327 A1 | 10/2004 | Doig et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0070995 A1 | 3/2005 | Zilla et al. |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0143802 A1 | 6/2005 | Soykan |
| 2005/0149166 A1 | 7/2005 | Schaeffer et al. |
| 2005/0154448 A1 | 7/2005 | Cully et al. |
| 2005/0171598 A1 | 8/2005 | Schaeffer |
| 2005/0203606 A1 | 9/2005 | VanCamp |
| 2005/0222649 A1 | 10/2005 | Capuano |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0266042 A1 | 12/2005 | Tseng |
| 2005/0283188 A1 | 12/2005 | Loshakove et al. |
| 2006/0015170 A1 | 1/2006 | Jones et al. |
| 2006/0030911 A1 | 2/2006 | Letort |
| 2006/0052799 A1 | 3/2006 | Middleman et al. |
| 2006/0069426 A1 | 3/2006 | Weinberger |
| 2006/0095104 A1 | 5/2006 | Magers |
| 2006/0100684 A1 | 5/2006 | Elliott |
| 2006/0106406 A1 | 5/2006 | Weinberger |
| 2006/0149360 A1 | 7/2006 | Schwammenthal |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0190070 A1* | 8/2006 | Dieck et al. ............ 623/1.12 |
| 2006/0193892 A1 | 8/2006 | Furst et al. |
| 2006/0212113 A1 | 9/2006 | Shaolian et al. |
| 2006/0229709 A1 | 10/2006 | Morris et al. |
| 2006/0241740 A1 | 10/2006 | Vardi et al. |
| 2006/0281966 A1 | 12/2006 | Peacock, III |
| 2007/0016281 A1* | 1/2007 | Melsheimer ............ 623/1.11 |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein et al. |
| 2007/0055326 A1* | 3/2007 | Farley et al. ............ 607/96 |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Menardiere et al. |
| 2007/0156167 A1 | 7/2007 | Connors et al. |
| 2007/0167898 A1 | 7/2007 | Peters et al. |
| 2007/0167955 A1 | 7/2007 | Menardiere et al. |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0239256 A1 | 10/2007 | Weber |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |

(56) References Cited

U.S. PATENT DOCUMENTS

| | | |
|---|---|---|
| 2008/0033527 A1 | 2/2008 | Nunez |
| 2008/0058918 A1 | 3/2008 | Watson |
| 2008/0064957 A1 | 3/2008 | Spence |
| 2008/0086193 A1 | 4/2008 | Thramann |
| 2008/0097578 A1 | 4/2008 | Erickson et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0140178 A1 | 6/2008 | Rasmussen |
| 2008/0147173 A1 | 6/2008 | McIff et al. |
| 2008/0167704 A1 | 7/2008 | Wright et al. |
| 2008/0176271 A1 | 7/2008 | Silver |
| 2008/0195190 A1 | 8/2008 | Bland et al. |
| 2008/0195191 A1 | 8/2008 | Luo et al. |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0300665 A1 | 12/2008 | Lootz et al. |
| 2008/0312732 A1 | 12/2008 | Hartley et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069882 A1 | 3/2009 | Venturelli et al. |
| 2009/0082841 A1 | 3/2009 | Zacharias et al. |
| 2009/0099640 A1 | 4/2009 | Weng |
| 2009/0099647 A1 | 4/2009 | Glimsdale et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0070019 A1 | 3/2010 | Shalev |
| 2010/0082091 A1 | 4/2010 | Berez et al. |
| 2010/0161025 A1 | 6/2010 | Kuppurathanam et al. |
| 2010/0161026 A1 | 6/2010 | Brocker et al. |
| 2010/0168838 A1 | 7/2010 | Hartley et al. |
| 2010/0211159 A1 | 8/2010 | Schmid et al. |
| 2010/0256725 A1 | 10/2010 | Rasmussen |
| 2010/0274187 A1 | 10/2010 | Argentine |
| 2010/0274345 A1 | 10/2010 | Rust |
| 2010/0292774 A1 | 11/2010 | Shalev |
| 2010/0318171 A1 | 12/2010 | Porter et al. |
| 2010/0318180 A1 | 12/2010 | Porter |
| 2011/0022149 A1 | 1/2011 | Cox |
| 2011/0022153 A1 | 1/2011 | Schreck et al. |
| 2011/0040366 A1 | 2/2011 | Goetz et al. |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval |
| 2011/0208298 A1 | 8/2011 | Tuval |
| 2011/0218607 A1 | 9/2011 | Arbefeuille et al. |
| 2011/0218609 A1 | 9/2011 | Chobotov et al. |
| 2011/0218617 A1 | 9/2011 | Nguyen et al. |
| 2011/0257725 A1 | 10/2011 | Argentine |
| 2011/0262684 A1 | 10/2011 | Wintsch |
| 2011/0264184 A1 | 10/2011 | Heltai |
| 2011/0288622 A1 | 11/2011 | Chan et al. |
| 2012/0143317 A1 | 6/2012 | Cam |
| 2012/0158038 A1 | 6/2012 | Leschinsky |
| 2013/0116773 A1 | 5/2013 | Roeder et al. |
| 2013/0158646 A1 | 6/2013 | Roeder |
| 2013/0274866 A1 | 10/2013 | Cox |
| 2013/0338753 A1 | 12/2013 | Geusen |
| 2014/0316510 A1 | 10/2014 | Berra |
| 2014/0364930 A1 | 12/2014 | Strauss |

FOREIGN PATENT DOCUMENTS

| | | |
|---|---|---|
| CN | 201058061 Y | 5/2008 |
| CN | 101980670 | 2/2011 |
| CN | 101998845 | 3/2011 |
| EP | 0893108 | 1/1999 |
| EP | 1 177 779 | 2/2002 |
| EP | 1177780 A2 | 2/2002 |
| EP | 1325716 A1 | 7/2003 |
| EP | 2 266 509 A1 | 12/2010 |
| EP | 2298248 A1 | 3/2011 |
| JP | 2000-279533 | 10/2000 |
| JP | 2002-253682 | 9/2002 |
| WO | 96/39104 | 12/1996 |
| WO | 99/25273 | 5/1999 |
| WO | 99/51165 | 10/1999 |
| WO | 02/083038 | 10/2002 |
| WO | 03/034948 | 5/2003 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2005/046524 | 5/2005 |
| WO | 2006/007389 | 1/2006 |
| WO | 2006/028925 | 3/2006 |
| WO | 2006/070372 | 7/2006 |
| WO | 2006/088905 | 8/2006 |
| WO | 2006/130755 | 12/2006 |
| WO | 2007/084547 | 7/2007 |
| WO | 2007115017 A1 | 10/2007 |
| WO | 2007/144782 | 12/2007 |
| WO | 2008/008291 | 1/2008 |
| WO | 2008/021557 | 2/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/051704 | 5/2008 |
| WO | 2008/053469 | 5/2008 |
| WO | 2008/066923 | 6/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/042210 | 4/2010 |
| WO | 2010/045238 | 4/2010 |
| WO | 2010/062355 | 6/2010 |
| WO | 2010/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |

(56) References Cited

FOREIGN PATENT DOCUMENTS

| WO | 2011/106533 | 9/2011 |
|---|---|---|
| WO | 2011/106544 | 9/2011 |
| WO | 2011/136930 | 11/2011 |
| WO | 2012/049679 | 4/2012 |
| WO | 2012/104842 | 8/2012 |
| WO | 2012/111006 | 8/2012 |
| WO | 2012/117395 | 9/2012 |

OTHER PUBLICATIONS

An English Translation of an Office Action dated Aug. 25, 2011, which issued during the prosecution of Chinese Patent Application No. 200880014919.9.

Fonseca A et al., "Intravascular ultrasound assessment of the novel AngioSculpt scoring balloon catheter for the treatment of complex coronary lesions," J Invasive Cardiol 20(1):21-7 (Jan. 2008).

An International Search Report and a Written Opinion both dated Sep. 24, 2012, which issued during the prosecution of Applicant's PCT/IL2012/000060.

Khlif H et al., "Contribution to the Improvement of Textile Vascular Prostheses Crimping," Trends in Applied Sciences Research 6(9):1019-1027 (2011).

An International Search Report and a Written Opinion both dated Jul. 13, 2012, which issued during the prosecution of Applicant's PCT/IL2012/000083.

An International Search Report and a Written Opinion both dated Jul. 17, 2012, which issued during the prosecution of Applicant's PCT/IL2012/000095.

An International Search Report and a Written Opinion both dated Aug. 31, 2012, which issued during the prosecution of Applicant's PCT/IL2012/000148.

An International Search Report and a Written Opinion both dated Sep. 6, 2012, which issued during the prosecution of Applicant's PCT/IL2012/000190.

An International Search Report and a Written Opinion both dated Jun. 19, 2012, which issued during the prosecution of Applicant's PCT/IL2012/000241.

An International Search Report and a Written Opinion both dated Nov. 27, 2012, which issued during the prosecution of Applicant's PCT/IL2012/000300.

An International Search Report and a Written Opinion both dated Feb. 4, 2011, which issued during the prosecution of Applicant's PCT/IB2010/052861.

An International Search Report and a Written Opinion both dated Sep. 29, 2008, which issued during the prosecution of Applicant's PCT/IL08/000287.

An International Search Report and a Written Opinion both dated Mar. 11, 2009, which issued during the prosecution of Applicant's PCT/IL2007/001312.

An International Search Report and a Written Opinion both dated Jun. 30, 2009, which issued during the prosecution of Applicant's PCT/IL2008/001621.

An International Search Report and a Written Opinion both dated Nov. 5, 2010, which issued during the prosecution of Applicant's PCTIL2010000549.

An International Search Report and a Written Opinion both dated Dec. 3, 2010, which issued during the prosecution of Applicant's PCT/IL2010/000564.

An International Search Report and a Written Opinion both dated Mar. 10, 2011, which issued during the prosecution of Applicant's PCT/IL2010/000917.

An International Search Report and a Written Opinion both dated Aug. 4, 2011, which issued during the prosecution of Applicant's PCT/IL2010/000999.

An International Search Report and a Written Opinion both dated Mar. 30, 2011, which issued during the prosecution of Applicant's PCT/IL2010/001018.

An International Search Report and a Written Opinion both dated Apr. 18, 2011, which issued during the prosecution of Applicant's PCT/IL2010/001037.

An International Search Report and a Written Opinion both dated May 23, 2011, which issued during the prosecution of Applicant's PCT/IL2010/001087.

An International Search Report and a Written Opinion both dated Jun. 28, 2011, which issued during the prosecution of Applicant's PCT/IL2011/000135.

An International Search Report dated Oct. 4, 2012, which issued during the prosecution of Applicant's PCT/IL2012/000269.

An Office Action dated Apr. 27, 2011, which issued during the prosecution of U.S. Appl. No. 12/447,684.

An Office Action dated Nov. 12, 2010, which issued during the prosecution of U.S. Appl. No. 12/447,684.

An Office Action dated Mar. 24, 2011, which issued during the prosecution of U.S. Appl. No. 12/529,936.

An Office Action dated Oct. 28, 2011, which issued during the prosecution of U.S. Appl. No. 12/529,936.

An Office Action dated Jun. 19, 2012, which issued during the prosecution of U.S. Appl. No. 12/808,037.

An Office Action dated Oct. 11, 2012, which issued during the prosecution of U.S. Appl. No. 13/031,871.

Ryhänen J., in "Biocompatibility evaluation of nickel-titanium shape memory metal alloy," Academic Dissertation, Faculty of Medicine, Department of Surgery, University of Oulu, Finland (May 1999).

International Search Report and Written Opinion dated Jun. 14, 2013 issued in PCT/IL2012/050506.

EP Search in Appl. No. 12855964.8, dated Jun. 12, 2014.

Non-final office action in U.S. Appl. No. 14/240,600, dated Jul. 30, 2014.

Non-final office action in U.S. Appl. No. 13/513,397, dated Aug. 12, 2015.

Final office action in U.S. Appl. No. 13/384,075, dated Sep. 23, 2015.

Non-final OA in U.S. Appl. No. 13/577,161, dated Oct. 2, 2015.

An International Search Report and Written Opinion issued on Nov. 26, 2013 in PCT/IL2013/050656.

A non-final Office Action issued on Feb. 28, 2014 in U.S. Appl. No. 13/512,778.

An International Search Report and a Written Opinion both dated Mar. 18, 2015, which issued during the prosecution of Applicant's PCT/IL2014/050973.

European Search Report for European Patent Application No. 12741804.4 dated Jun. 30, 2014.

Communication dated Sep. 4, 2014, from the U.S. Patent and Trademark Office in counterpart U.S. Appl. No. 13/519,971.

An Office Action dated Dec. 9, 2015, which issued during the prosecution of U.S. Appl. No. 14/416,236.

European Search Report dated Jan. 18, 2016 which issued during the prosecution of Applicant's European App No. 10799521.9.

An Office Action dated Feb. 1, 2016, which issued during the prosecution of U.S. Appl. No. 14/241,793.

An International Search Report and a Written Opinion both dated Feb. 17, 2016, which issued during the prosecution of Applicant's PCT/IL2015/051221.

An Office Action dated Feb. 23, 2016, which issued during the prosecution of U.S. Appl. No. 14/416,236.

An Office Action dated Mar. 7, 2016, which issued during the prosecution of U.S. Appl. No. 14/240,600.

European Search Report dated Mar. 11, 2016 which issued during the prosecution of Applicant's European App No. 11739497.3.

An Invitation to pay additional fees dated Apr. 12, 2016, which issued during the prosecution of Applicant's PCT/IL2016/050014.

European Search Report dated Mar. 15, 2016 which issued during the prosecution of Applicant's European App No. 13825456.0.

An Office Action dated Mar. 28, 2016, which issued during the prosecution of U.S. Appl. No. 14/362,194.

Scurr et al., "Fenestrated Aortic Stent Grafts," Semin Intervent Radiol. Jun. 2007; 24(2): 211-220.

An Office Action dated Apr. 14, 2016, which issued during the prosecution of Canadian Patent Application No. 2,766,347.

(56) References Cited

OTHER PUBLICATIONS

European Search Report dated May 23, 2016 which issued during the prosecution of Applicant's European App No. 10832752.9.

An International Search Report and a Written Opinion both dated Jun. 21, 2016, which issued during the prosecution of Applicant's PCT/IL2016/050014.

An Office Action dated Jul. 22, 2016, which issued during the prosecution of Chinese Patent Application No. 201480012648.9.

An Office Action dated Aug. 3, 2016, which issued during the prosecution of U.S. Appl. No. 14/241,793.

* cited by examiner

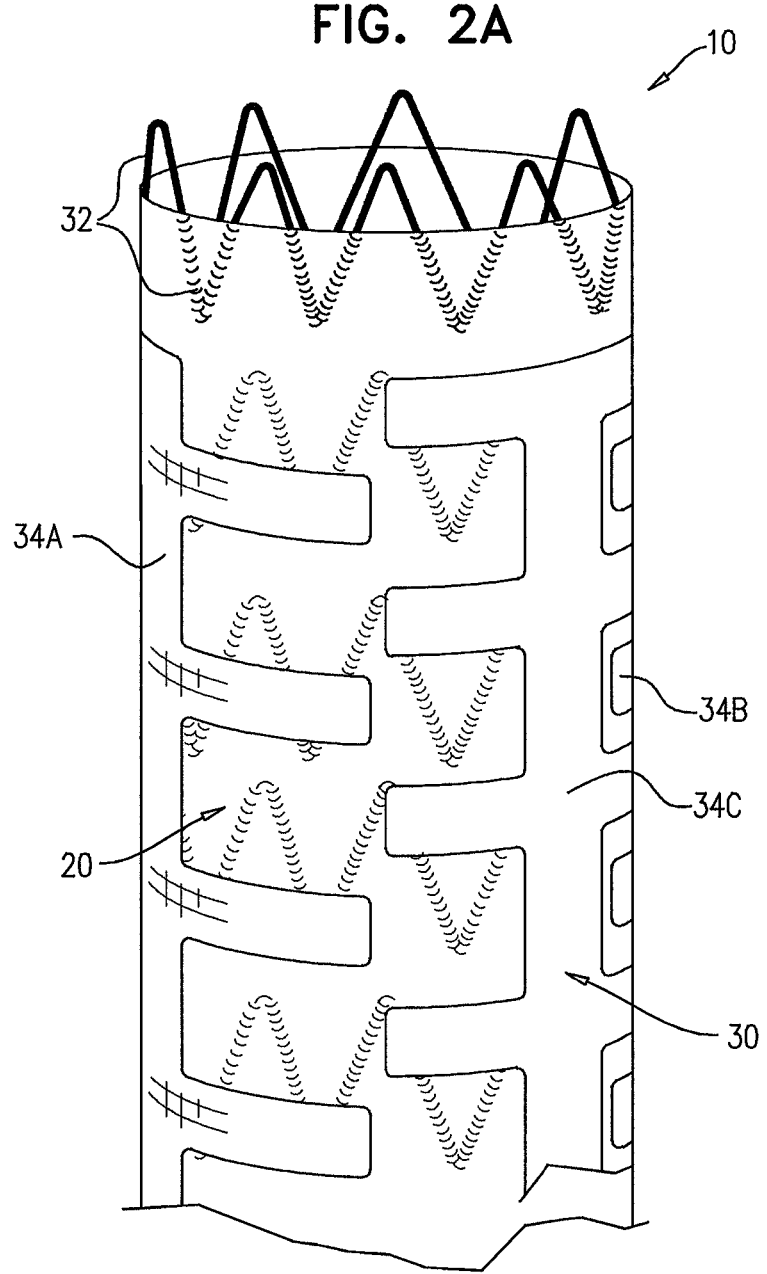

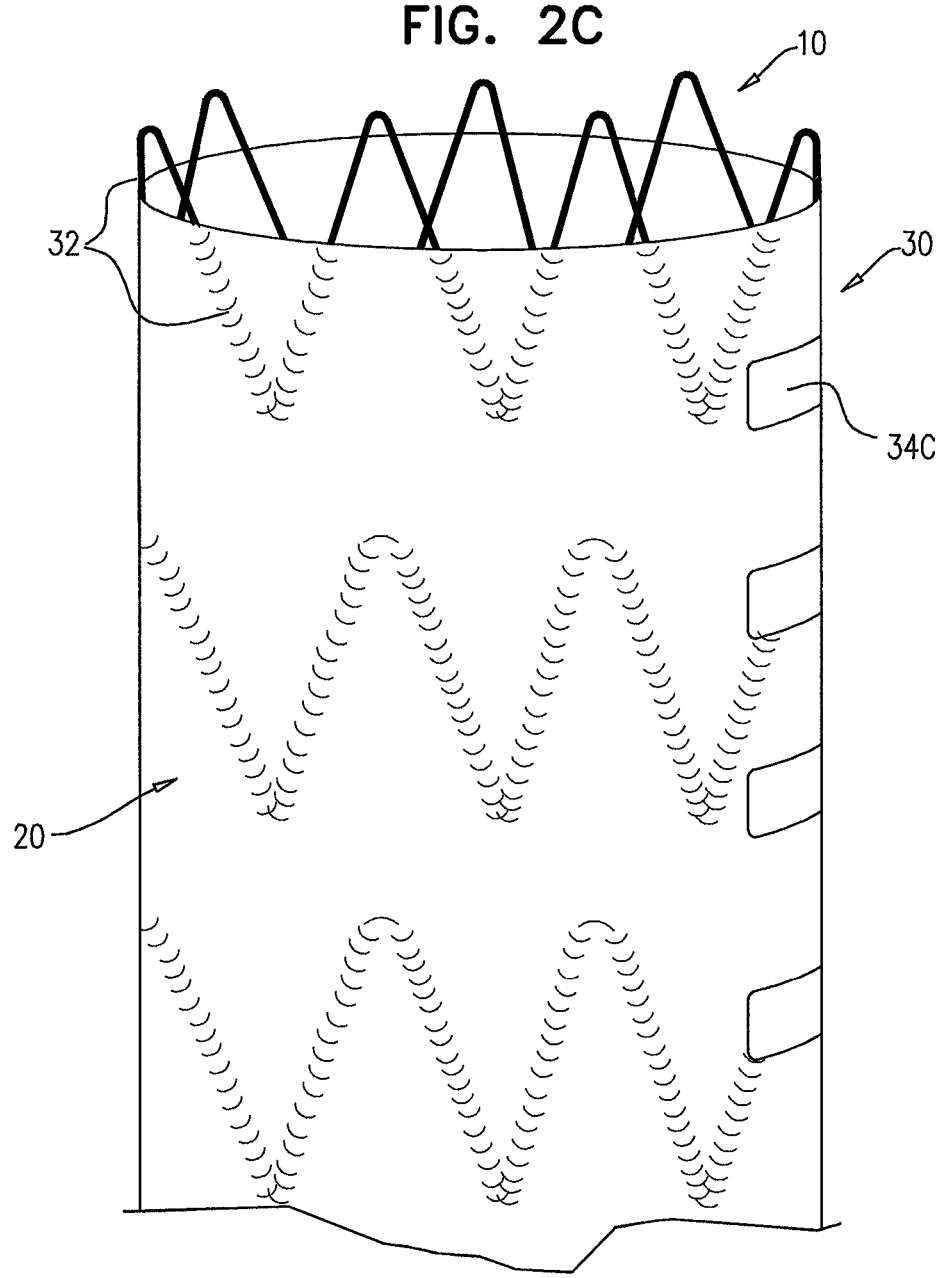

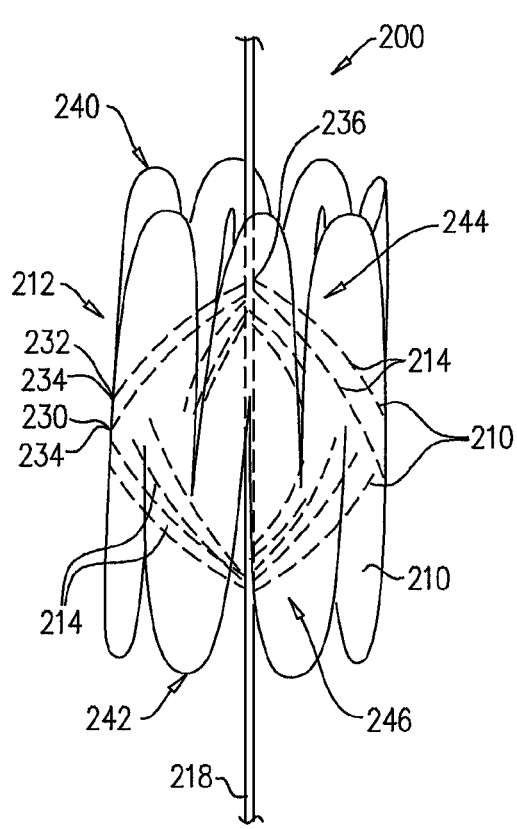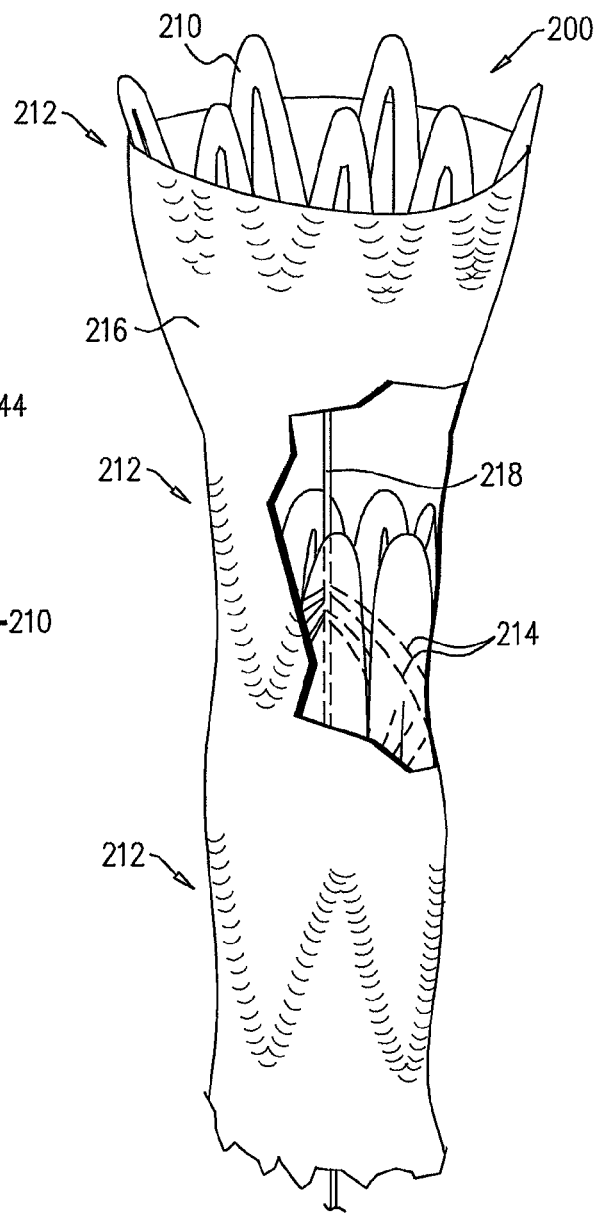

IMPLANTABLE MEDICAL DEVICES CONSTRUCTED OF SHAPE MEMORY MATERIAL

CROSS-REFERENCES TO RELATED APPLICATIONS

The present patent application claims priority from U.S. Provisional Application 61/438,977, filed Feb. 3, 2011, which is assigned to the assignee of the present application and is incorporated herein by reference.

FIELD OF THE APPLICATION

The present invention relates generally to implantable medical devices, and specifically to delivery tools and implantable medical devices comprising a shape memory material.

BACKGROUND OF THE APPLICATION

Some materials, both organic and metallic, have shape memory. An article made of such materials when deformed "remembers" its original, cold-forged shape, and returns to its pre-deformed shape when heated. The three main shape memory alloys are copper-zinc-aluminum-nickel, copper-aluminum-nickel, and nickel-titanium (NiTi). NiTi shape memory alloys have two different temperature-dependent crystal structures (phases) called "martensite" (lower temperature) and austenite (higher temperature or parent phase). Several properties of austenite NiTi and martensite NiTi are notably different.

When heated, martensite NiTi begins to transform into austenite at a temperature called the austenite start temperature ($A_s$), and completes the transformation at a temperature called the austenite finish temperature ($A_f$). When cooled, austenite NiTi begins to transform into martensite at a temperature that is called the martensite start temperature ($M_s$), and is again completely reverted at a temperature called the martensite finish temperature ($M_f$).

Composition and metallurgical treatments have dramatic impacts on the above-mentioned transition temperatures. For practical applications, NiTi can have three different forms: martensite, stress-induced martensite (superelastic), and austenite. When the material is in its martensite form, it is soft and ductile and can be easily deformed (somewhat like soft pewter). Superelastic NiTi is highly elastic (rubber-like), while austenitic NiTi is quite strong and hard (similar to titanium).

NiTi has all of these properties, and their specific expression depends on the temperature in which the NiTi is used.

The temperature range for the martensite-to-austenite transformation, i.e., soft-to-hard transition, that takes place upon heating is somewhat higher than that for the reverse transformation upon cooling. The difference between the transition temperatures upon heating and cooling is called hysteresis (denoted as H). Hysteresis is generally defined as the difference between the temperatures at which the material is 50% transformed to austenite upon heating and 50% transformed to martensite upon cooling. This difference can be up to 20-30 degrees C. In practice, this means that an alloy designed to be completely transformed by body temperature upon heating ($A_f$<37 degrees C.) would require cooling to about +5 degrees C. to fully retransform into martensite ($M_f$).

One of the commercial uses of shape memory alloy exploits the pseudo-elastic properties of the metal during the high-temperature (austenitic) phase. This is the result of pseudoelasticity; the martensitic phase is generated by stressing the metal in the austenitic state and this martensite phase is capable of large strains. With the removal of the load, the martensite transforms back into the austenite phase and resumes its original shape. This allows the metal to be bent, twisted and pulled, before reforming its shape when released. This means the frames of shape memory alloy glasses are claimed to be "nearly indestructible" because it appears no amount of bending results in permanent plastic deformation.

The martensite temperature of shape memory alloys is dependent on a number of factors including alloy chemistry. Shape memory alloys with transformation temperatures in the range of 60-1450 K have been made.

Many shape memory alloys (SMAs) are known to display stress-induced martensite (SIM). When an SMA sample exhibiting stress-induced martensite is stressed at a temperature above $M_s$ (so that the austenitic state is initially stable), but below $M_d$ (the maximum temperature at which martensite formation can occur even under stress) it first deforms elastically and then, at a critical stress, begins to transform by the formation of stress-induced martensite. Depending on whether the temperature is above or below $A_s$, the behavior when the deforming stress is released differs. If the temperature is below $A_s$, the stress-induced martensite is stable; but if the temperature is above $A_s$, the martensite is unstable and transforms back to austenite, with the sample returning (or attempting to return) to its original shape. The effect is seen in almost all alloys which exhibit a thermoelastic martensitic transformation, along with the shape memory effect. However, the extent of the temperature range over which SIM is seen and the stress and strain ranges for the effect vary greatly with the alloy.

Ryhänen J, in "Biocompatibility evaluation of nickel-titanium shape memory metal alloy," Academic Dissertation, Faculty of Medicine, Department of Surgery, University of Oulu, Finland (May 1999), which is incorporated herein by reference, describes the shape memory effect, superelasticity, and good damping properties that make the nickel-titanium shape memory metal alloy (Nitinol or NiTi) a fascinating material for surgical applications. Among other things, the dissertation describes the mechanical properties of NiTi in Section 2.3.8, including Table I thereof.

SUMMARY OF THE APPLICATION

Some applications of the present invention provide medical apparatus comprising a hollow placement device and a stent body restrained therein. The placement device comprises a restraining member, which is configured to rotatively release the stent body therefrom. Unlike in some conventional techniques for deploying a stent body, in some applications of the present invention an outer tube need not be axially withdrawn in order to release the stent body. Therefore, in some applications of the present invention a proximal stopper is not needed to prevent the stent body from being withdrawn proximally as the outer tube is withdrawn. The stent body thus is less likely to fold or otherwise become distorted during deployment.

The medical apparatus comprises structural stent elements, at least a portion of which define the stent body. The stent body is configured to assume radially-compressed and radially-expanded states. For some applications, the medical apparatus further comprises an implantable-grade fabric securely attached to and at least partially covering the stent body.

At least a portion of stent body is initially disposed, while in the radially-compressed state, in the restraining member. The restraining member is configured to assume at least (a) a first rotational state, in which the restraining member restrains the at least a portion of the stent body in the radially-compressed state, and (b) a second rotational state, in which the restraining member releases the at least a portion of the stent body, thereby allowing the at least a portion of the stent body to transition to the radially-expanded state.

For some applications, the restraining member comprises at least two generally arcuate sections, which together define at least a circumferential portion of a generally tubular structure. The restraining member is configured such that (a) when the restraining member is in the first rotational state, the arcuate sections are rotationally disposed with respect to each other around a central longitudinal axis of the restraining member so as to restrain the at least a portion of the stent body in the radially-compressed state; and (b) when the restraining member is in the second rotational state, the arcuate sections are rotationally disposed with respect to each other around the axis so as to not restrain the stent body within the restraining member, thereby releasing the stent body from the restraining member and allowing the at least a portion of the stent body to transition to the radially-expanded state.

Some applications of the present invention provide another medical apparatus comprising structural stent elements, at least a portion of which are shaped so as to define (a) one or more generally circumferential bands, and (b) a plurality of engagement members that are joined to and extend radially inwardly from each of the bands. For some applications, the structural stent elements, including the at least a portion that defines the one or more bands, are shaped so as to define a generally tubular structure. For some applications, the medical apparatus further comprises an implantable-grade fabric securely attached to and at least partially covering the generally tubular structure.

The medical apparatus further comprises an elongated latch member which is threaded through the engagement members, thereby physically latching engagement members. Typically, the elongated latch member comprises a wire or a hollow tube. The engagement members and each of the one or more bands are configured such that (a) when the latch member is threaded through and thus physically latching the engagement members, the engagement members retain the band in a radially-compressed state; and (b) when the latch member is removed from the engagement members, the band assumes a radially-expanded state.

For some applications, the engagement members have (a) respective first ends, which are joined to and extend from one of one or more bands, (b) respective second ends, which are joined to and extend from the band at respective junctions, and (c) respective curved portions between the respective first and the respective second ends. When the latch member is threaded through the engagement members, the curved portions pass around the latch member. As a result, the latch member holds the curved portions near a central longitudinal axis of the band. The engagement members thus prevent the band from expanding radially.

For some of the applications described above, the structural stent elements comprise a shape memory alloy. For example, the shape memory alloy may comprise a nickel and titanium, and, optionally, additionally cobalt. The shape memory element may comprise any shape memory alloy known in the art that is characterized by a stress-induced martensitic state and an unstressed austenitic state. For some applications, suitable alloys are those that display stress-induced martensite at temperatures near mammalian (e.g., human) body temperature (35-40 degrees C.).

There is therefore provided, in accordance with an application of the present invention, medical apparatus for insertion into a mammalian body, the apparatus including:
structural stent elements, at least a portion of which are shaped so as to define:
at least one generally circumferential band, and
a plurality of engagement members that are joined to and extend radially inwardly from the band; and
an elongated latch member which is threaded through the engagement members, thereby physically latching the engagement members,
wherein the band and the engagement members are configured such that:
when the latch member is threaded through and thus physically latches the engagement members, the engagement members retain the band in a radially-compressed state, and
when the latch member is removed from the engagement members, the band assumes a radially-expanded state.

For some applications, the elongated latch member includes an element selected from the group consisting of: a wire and a hollow tube.

For some applications, the engagement members have (a) respective first ends, which are joined to and extend from the band, (b) respective second ends, which are joined to and extend from the band at respective junctions, and (c) respective curved portions between the respective first and the respective second ends. For some applications, the circumferential band has distal and proximal ends, and all of the engagement members are shaped such that the curved portions are disposed more proximally than the junctions, when the latch member physically latches the engagement members. Alternatively, for some applications, the circumferential band has distal and proximal ends, and wherein, when the latch member physically latches the engagement members: a first subset of the engagement members are shaped such that the curved portions thereof are disposed more distally than the junctions thereof, a second subset of the engagement members are shaped such that the curved portions thereof are disposed more proximally than the junctions thereof, and the first and the second subsets do not include any common engagement members.

For any of the applications described above, the at least a portion of the structural stent elements may be shaped so as to define a plurality of generally circumferential bands, and respective subsets of the engagement members are joined to and extend radially inwardly from the bands.

For any of the applications described above, at least a portion of the structural stent elements of the band may be arranged as a plurality of pairs of two respective generally straight, adjacently disposed structural stent elements joined by respective peaks, and each of the engagement members may have (a) a first end, which is joined to and extends from one of the generally straight structural stent elements of one of the pairs, (b) a second end, which is joined to and extends from the other of the generally straight structural stent elements of the one of the pairs, and (c) a curved portion between the first and the second ends of the engagement member. For some applications, the latch member, when physically latching the engagement members, rests against an inner surface of the curved portion.

For any of the applications described above, the structural stent elements, including the at least a portion that defines the at least one band, may be shaped so as to define a generally tubular structure, and the medical apparatus further includes an implantable-grade fabric securely attached to and at least partially covering the generally tubular structure.

For any of the applications described above, the apparatus may further include a hollow, elongated delivery shaft, in which the at least one band is initially positioned, with the latch member threaded through the engagement members. For some applications, the delivery shaft and the at least one band are configured such that the at least one band, when retained by the latch member in the radially-compressed state, is slidably positioned in the delivery shaft. Alternatively, for some applications, the radially-compressed state is a first radially-compressed state, and the delivery shaft and the at least one band are configured such that the delivery shaft holds the at least one band in a second radially-compressed state that is more radially compressed than the first radially-compressed state.

For any of the applications described above, the structural stent elements may include a shape memory alloy. For some applications, the shape memory alloy includes nickel and titanium, and, optionally, further includes cobalt.

For some applications, (a) the shape memory alloy includes a pseudoelastic shape-memory alloy, the alloy displaying reversible stress-induced martensite at between 35 and 40 degrees C. such that it has a stress-induced martensitic state and an austenitic state; (b) when the alloy is in the stress-induced martensitic state, the band has a deformed shape that provides the radially-compressed state; and (c) when the alloy is in the austenitic state, the band has a different unstressed shape that provides the radially-expanded state.

For some applications, the band and the engagement members are configured such that:

when the latch member physically latches the engagement members and the shape memory alloy is at a temperature greater than an austenite start temperature of the shape memory alloy, the latch member retains the shape memory alloy of the band so that at least a portion of the alloy is in at least a partially stress-induced martensitic state and the band is in the deformed shape, and when the latch member is removed from the plurality of engagement members and the shape memory alloy is at a temperature greater than the austenite start temperature, at least a portion of the shape memory alloy at least partially transitions to an austenitic state from the stress-induced martensitic state, thereby causing a transformation of the band from the deformed shape to the unstressed shape.

For some applications, the shape memory alloy is realized such that the transformation occurs without any change in temperature of the latch member or the shape memory alloy. Alternatively, for some applications, the shape memory alloy is realized such that the transformation occurs with a change in temperature of at least one element selected from group consisting of: the latch member and the shape memory alloy.

For some applications, the latch member is configured to function as a heat dissipation element, which is in physical contact with the shape memory alloy at least when the latch member physically latches the engagement members. For some applications, the latch member, when physically latching the engagement members, is disposed adjacent to at least a portion of the shape memory alloy. For some applications, the latch member, when physically latching the engagement members, is in direct physical contact with at least a portion of the shape memory alloy.

For some applications, the apparatus further includes a heat dissipation element, which is in thermal contact with the shape memory alloy at least when the band is in the radially-compressed state. For some applications, the apparatus further includes a hollow, elongated delivery shaft, in which the at least one band is initially positioned, retained by the latch member in the radially-compressed state, and the elongated delivery shaft includes the heat dissipation element.

For some applications, the heat dissipation element is disposed adjacent to at least part of the shape memory alloy while the shape memory alloy is in the stress-induced martensitic state.

For some applications, the heat dissipation element includes a plurality of heat dissipation elements.

For some applications, the heat dissipation element is adapted to lose thermal energy at a rate faster than the rate of change of thermal energy caused by the change in temperature.

There is further provided, in accordance with an application of the present invention, a method including:

providing (a) structural stent elements, at least a portion of which are shaped so as to define (i) at least one generally circumferential band, and (ii) a plurality of engagement members that are joined to and extend radially inwardly from the band, and (b) an elongated latch member which is threaded through the engagement members, thereby physically latching the engagement members;

transvascularly introducing the at least one band into a blood vessel of a mammalian subject while the latch member is threaded through and thus physically latches the engagement members, such that the engagement members retain the band in a radially-compressed state; and thereafter, removing the latch member from the engagement members, thereby transitioning the band to a radially-expanded state.

For some applications, providing the latch member includes providing a latch member that includes an element selected from the group consisting of: a wire and a hollow tube.

For some applications, providing the engagement members includes providing engagement members that have (a) respective first ends, which are joined to and extend from the band, (b) respective second ends, which are joined to and extend from the band at respective junctions, and (c) respective curved portions between the respective first and the respective second ends.

For some applications, the structural stent elements, including the at least a portion that defines the at least one band, are shaped so as to define a generally tubular structure, and further including providing an implantable-grade fabric securely attached to and at least partially covering the generally tubular structure.

For some applications, transvascularly introducing includes transvascularly introducing the at least one band while the at least one band is positioned in a hollow, elongated delivery shaft, with the latch member threaded through the engagement members.

For some applications, transvascularly introducing includes advancing the delivery shaft to a target site in the blood vessel, and thereafter sliding the at least one band through at least a portion of the delivery shaft while the at least one band is retained by the latch member in the radially-compressed state.

For some applications, the radially-compressed state is a first radially-compressed state, and transvascularly introducing includes:

transvascularly introducing delivery shaft while the delivery shaft holds the at least one band in a second radially-compressed state that is more radially compressed than the first radially-compressed state; and thereafter, withdrawing the delivery shaft so as to release the at least one band from the delivery shaft, thereby causing the at least one band to radially expand to the first radially-compressed state.

For some applications, providing the structural stent elements includes providing structural stent elements that include a shape memory alloy.

There is still further provided, in accordance with an application of the present invention, medical apparatus for insertion into a mammalian body, the apparatus including:

structural stent elements, at least a portion of which define a stent body that is configured to assume radially-compressed and radially-expanded states; and a restraining member, in which at least a portion of the stent body is disposed in the radially-compressed state, and which restraining member is configured to assume at least:

a first rotational state, in which the restraining member restrains the at least a portion of the stent body in the radially-compressed state, and a second rotational state, in which the restraining member releases the at least a portion of the stent body, thereby allowing the at least a portion of the stent body to transition to the radially-expanded state.

For some applications, the restraining member includes at least two generally arcuate sections, which together define at least a circumferential portion of a generally tubular structure, and wherein:

when the restraining member is in the first rotational state, the arcuate sections are rotationally disposed with respect to each other around a central longitudinal axis of the restraining member so as to restrain the at least a portion of the stent body in the radially-compressed state, and when the restraining member is in the second rotational state, the arcuate sections are rotationally disposed with respect to each other around the axis so as to not restrain the stent body within the restraining member, thereby releasing the stent body from the restraining member and allowing the at least a portion of the stent body to transition to the radially-expanded state.

For some applications, when the restraining member is in the first rotational state, circumferentially-adjacent ones of the arcuate sections partially circumferentially overlap one another along at least portions of respective axial lengths of the arcuate sections. For some applications, when the restraining member is in the first rotational state, the circumferentially-adjacent ones of the arcuate sections circumferentially overlap one another along less than respective entire axial lengths of portions of the arcuate sections that restrain the at least a portion of the stent body.

For some applications, when the restraining member is in the second rotational state, the arcuate sections circumferentially overlap one another to a greater extent than when in the first rotational state. For some applications, when the restraining member is in the first rotational state, the arcuate sections do not circumferentially overlap one another.

For some applications, when the restraining member is in the first rotational state, a greatest arc between circumferentially-adjacent ones of the arcuate sections, along respective entire axial lengths of portions of the arcuate sections that restrain the at least a portion of the stent body, is no more than 150 degrees. For some applications, when the restraining member is in the first rotational state, the greatest arc between circumferentially-adjacent ones of the arcuate sections is no more than 120 degrees.

For some applications, the restraining member includes exactly three generally arcuate sections. For some applications, the restraining member includes between two and six generally arcuate sections.

For some applications, when the restraining member is in the first rotational state, the arcuate sections collectively circumscribe one or more arcs having an angular sum of at least 220 degrees. For some applications, the angular sum equals 360 degrees.

For some applications, when the restraining member is in the second rotational state, the arcuate sections collectively circumscribe one or more arcs having an angular sum of no more than 150 degrees, such as no more than 90 degrees.

For some applications, the arcuate sections are shaped so as to define (a) respective longitudinal base strips, and (b) respective pluralities of circumferential tabs that extend circumferentially from the respective longitudinal base strips, and wherein, when the restraining member is in the first rotational state, the longitudinal base strips of circumferentially-adjacent ones of the arcuate sections do not circumferentially overlap one another, and the circumferential tabs overlap the longitudinal base strips of circumferentially-adjacent ones of the arcuate sections. For some applications, when the restraining member is the second rotational state, the longitudinal base strips of at least some of the arcuate sections at least partially overlap one another. For some applications, when the restraining member is the second rotational state, the longitudinal base strips of all of the arcuate sections at least partially overlap one another.

For some applications, portions of the arcuate sections that restrain the at least a portion of the stent body in the radially-compressed state have respective lengths along the axis, and an average of the lengths is at least 30% of an average length of the at least a portion of the stent body when in the radially-compressed state.

For any of the applications described above, a portion of the restraining element that restrains the at least a portion of stent body 20 in the radially-compressed state may have a length along the axis of at least 30% of an average length of the at least a portion of the stent body when in the radially-compressed state.

For any of the applications described above, the apparatus may further include an implantable-grade fabric securely attached to and at least partially covering the stent body.

For any of the applications described above, the structural stent elements may include a shape memory alloy. For some applications, the shape memory alloy includes nickel and titanium, and, optionally further includes cobalt.

For some applications, (a) the shape memory alloy includes a pseudoelastic shape-memory alloy, the alloy displaying reversible stress-induced martensite at between 35 and 40 degrees C. such that it has a stress-induced martensitic state and an austenitic state, (b) when the alloy is in the stress-induced martensitic state, the stent body has a deformed shape that provides the radially-compressed state, and (c) when the alloy is in the austenitic state, the stent body has a different unstressed shape that provides the radially-expanded state. For some applications, when the restraining member is in the first rotational state and the shape memory alloy is at a temperature greater than an austenite start temperature of the shape memory alloy, the restraining member confines and stresses the memory alloy element so that the at least a portion of the stent body is retained in a stress-induced martensite state. For some applications, when the at least a portion of the stent body is released and transitions to the radially-expanded state, the transformation of the stent body occurs with a change in the temperature of at least one element from the group consisting of: the restraining member, the structural stent elements including the shape memory alloy, and the mammalian body. For some applications, the apparatus further includes a heat dissipation element in thermal contact with at least one element selected from the group consisting of: the restraining member and the structural stent elements.

There is additionally provided, in accordance with an application of the present invention, a method including:

providing (a) structural stent elements, at least a portion of which define a stent body that is configured to assume radially-compressed and radially-expanded states, and (b) a restraining member, in which at least a portion of the stent body is disposed in the radially-compressed state;

transvascularly introducing the stent body into a blood vessel of a mammalian subject while the restraining member is in a first rotational state, in which the restraining member restrains the at least a portion of the stent body in the radially-compressed state; and thereafter, causing the restraining member to assume a second rotational state, so that the restraining member releases the at least a portion of the stent body, thereby allowing the at least a portion of the stent body to transition to the radially-expanded state.

For some applications, providing the restraining member includes providing a restraining member that includes at least two generally arcuate sections, which together define at least a circumferential portion of a generally tubular structure, and (a) when the restraining member is in the first rotational state, the arcuate sections are rotationally disposed with respect to each other around a central longitudinal axis of the restraining member so as to restrain the at least a portion of the stent body in the radially-compressed state, and (b) when the restraining member is in the second rotational state, the arcuate sections are rotationally disposed with respect to each other around the axis so as to not restrain the stent body within the restraining member, thereby releasing the stent body from the restraining member and allowing the at least a portion of the stent body to transition to the radially-expanded state.

For some applications, when the restraining member is in the first rotational state, circumferentially-adjacent ones of the arcuate sections partially circumferentially overlap one another along at least portions of respective axial lengths of the arcuate sections. For some applications, when the restraining member is in the first rotational state, the circumferentially-adjacent ones of the arcuate sections circumferentially overlap one another along less than respective entire axial lengths of portions of the arcuate sections that restrain the at least a portion of the stent body.

For some applications, when the restraining member is in the second rotational state, the arcuate sections circumferentially overlap one another to a greater extent than when in the first rotational state. For some applications, when the restraining member is in the first rotational state, the arcuate sections do not circumferentially overlap one another.

For some applications, the method further includes providing an implantable-grade fabric securely attached to and at least partially covering the stent body.

For some applications, providing the structural stent elements includes providing structural stent elements that include a shape memory alloy.

The present invention will be more fully understood from the following detailed description of embodiments thereof, taken together with the drawings, in which:

BRIEF DESCRIPTION OF THE DRAWINGS

FIGS. 2A-C are schematic illustrations of the medical apparatus of FIGS. 1A and 1B in several respective rotational states, in accordance with an application of the present invention;

FIGS. 5A and 5B are schematic illustrations of yet another medical apparatus, in accordance with respective applications of the present invention.

DETAILED DESCRIPTION OF EMBODIMENTS

Figure 1A:
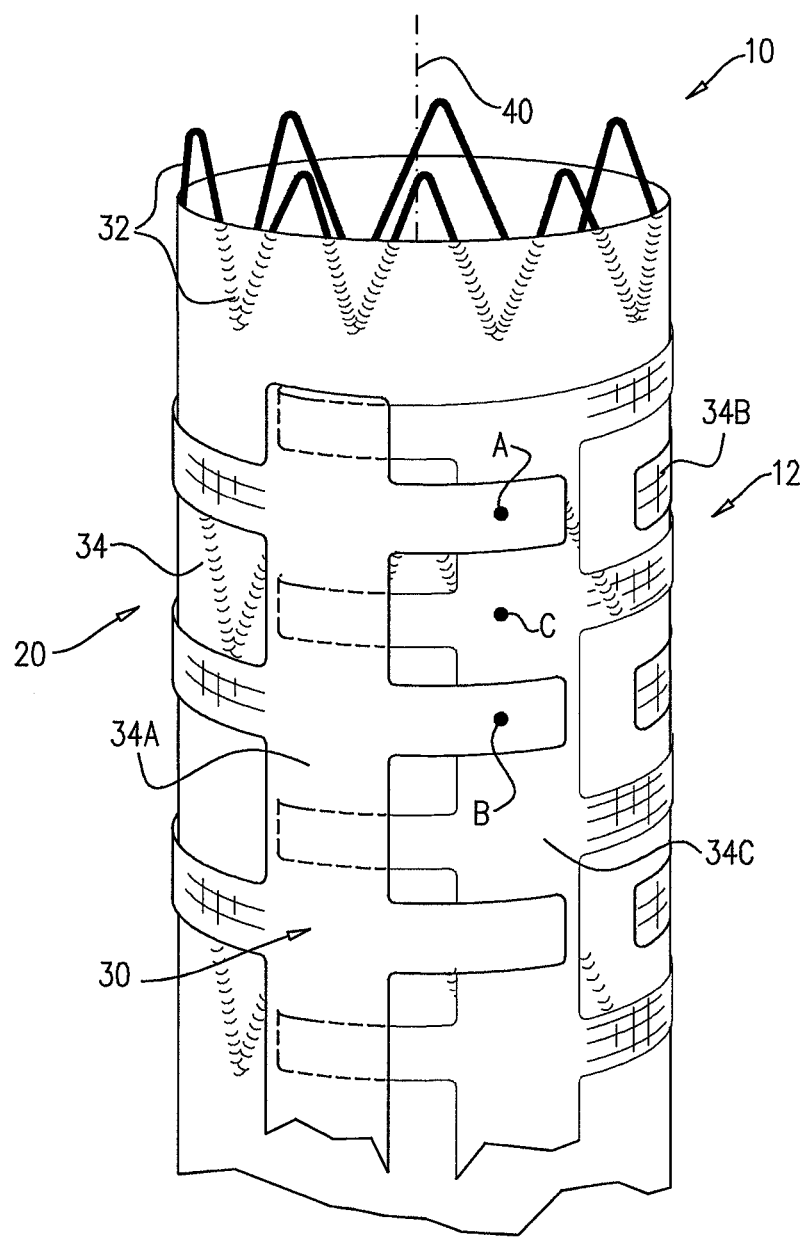
FIG. 1A is a schematic illustrations of medical apparatus comprising a hollow placement device and a stent body restrained therein, in accordance with an application of the present invention.
Figure 1B:
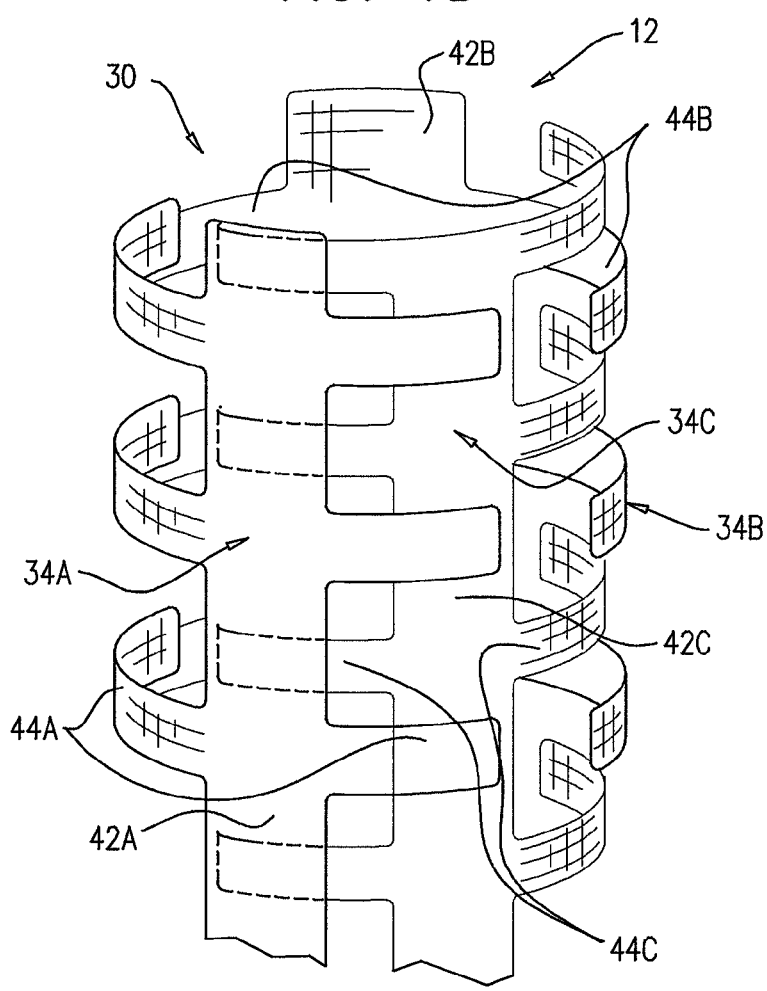
FIG. 1B shows the hollow placement device of FIG. 1A without the stent body restrained therein, in accordance with an application of the present invention.

FIG. 1A is a schematic illustrations of medical apparatus 10 comprising a hollow placement device 12 and a stent body 20 restrained therein, in accordance with an application of the present invention. FIG. 1B shows hollow placement device 12 without stent body 20 restrained therein, in accordance with an application of the present invention. Medical apparatus 10 is configured for insertion into a mammalian body, such as a human body. Placement device 12 comprises a restraining member 30, which is configured to rotatively release stent body 20 therefrom, as described hereinbelow.

As shown in FIG. 1A, medical apparatus 10 comprises structural stent elements 32, at least a portion of which define stent body 20. Stent body 20 is configured to assume radially-compressed and radially-expanded states. Stent body 20 is shown in the radially-compressed state in FIG. 1A (as well as in FIGS. 2A-B, described hereinbelow). For some applications, medical apparatus 10 further comprises an implantable-grade fabric 34 securely attached to and at least partially covering stent body 20 (an inner and/or an outer surface of the stent body). The fabric typically defines a fluid flow guide through the body of the stent. The fabric is biologically-compatible and substantially blood-impervious, and may comprise, for example, a polyester, a polyethylene (e.g., a poly-ethylene-terephthalate), a polymeric film material (e.g., polytetrafluoroethylene), a polymeric textile material (e.g., woven polyethylene terephthalate (PET)), natural tissue graft (e.g., saphenous vein or collagen), or a combination thereof.

Also as shown in FIG. 1A, at least a portion of stent body 20 is initially disposed, while in the radially-compressed state, in restraining member 30.

Restraining member 30 is configured to assume at least:
a first rotational state, in which restraining member 30 restrains the at least a portion of stent body 20 in the radially-compressed state, and
a second rotational state, in which restraining member 30 releases the at least a portion of stent body 20, thereby allowing the at least a portion of stent body 20 to transition to the radially-expanded state.

Restraining member 30 typically can assume many additional rotational states, some of which restrain the stent body, some of which do not, and, optionally, some of which partially restrain the stent body. By way of example, restraining member 30 is shown in one first rotational state in FIGS. 1A and 1B, and two other first rotational states in FIGS. 2A and 2B. Also by way of example, restraining member 30 is shown in one second rotational state in FIG. 2C.

For some applications, restraining member 30 comprises at least two generally arcuate sections 34, which together define at least a circumferential portion of a generally tubular structure 36. Typically, restraining member 30 comprises between two and six generally arcuate sections 34, such as exactly three generally arcuate sections 34A, 34B, and 34C, as shown. Restraining member 30 is configured such that:

when restraining member 30 is in the first rotational state, arcuate sections 34 are rotationally disposed with respect to each other around a central longitudinal axis 40 of restraining member 30 so as to restrain the at least a portion of stent body 20 in the radially-compressed state, such as shown in FIG. 1A; and when restraining member 30 is in the second rotational state, arcuate sections 34 are rotationally disposed with respect to each other around axis 40 so as to not restrain stent body 20 within restraining member 30, thereby releasing stent body 20 from restraining member 30 and allowing the at least a portion of stent body 20 to transition to the radially-expanded state, such as shown in FIG. 2C, described hereinbelow.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

Figure 1C:
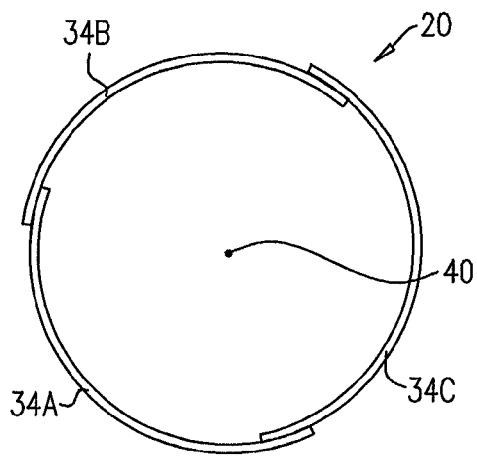
FIGS. 1C and 1D are schematic illustrations of the restraining member of FIGS. 1A and 1B viewed from one end of the restraining member, in accordance with an application of the present invention.
Figure 1D:
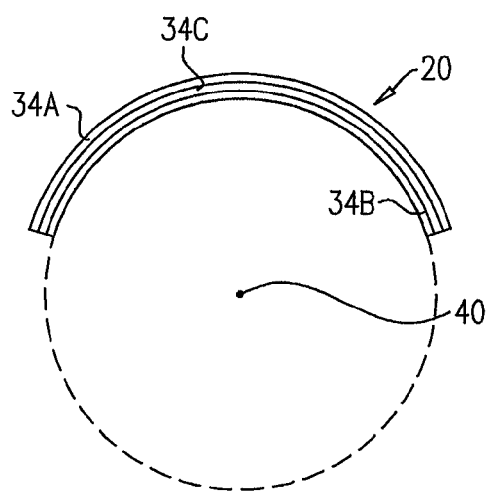

Reference is additionally made to FIGS. 1C and 1D, which are schematic illustrations of restraining member 30 viewed from one end of the restraining member, in accordance with an application of the present invention. FIG. 1C shows the restraining member in one first rotational state, while FIG. 1D shows the restraining member in one second rotational state.

For some applications, when restraining member 30 is in the first rotational state, circumferentially-adjacent ones of arcuate sections 34 partially circumferentially overlap one another along at least portions of respective axial lengths of the arcuate sections, such as shown in FIGS. 1A and 1B (and in FIG. 1D, except that the axial lengths are not shown). For some applications, when restraining member 30 is in the first rotational state, the circumferentially adjacent ones of the arcuate sections circumferentially overlap one another along less than respective entire axial lengths of portions of the arcuate sections that restrain the at least a portion of stent body 20, as shown in FIG. 1A. For example, as shown in FIG. 1A, circumferentially-adjacent arcuate sections 34A and 34C circumferentially overlap one another at points A and B along the axial lengths of arcuate sections 34A and 34C, but not at point C along these axial lengths.

Alternatively, for other applications, when restraining member 30 is in the first rotational state, arcuate sections 34 do not circumferentially overlap one another (configuration not shown); in this configuration, the arcuate sections are nevertheless distributed around axis 40 so as to restrain the at least a portion of stent body 20 in the radially-compressed state. For these latter applications, when restraining member 30 is in the first rotational state, a greatest arc between circumferentially-adjacent ones of the arcuate sections, along respective entire axial lengths of portions of the arcuate sections that restrain the at least a portion of the stent body (i.e., between the most circumferentially extreme portions of each arcuate section, at which circumferential locations no portion of any arcuate section is disposed), is no more than 150 degrees, such as no more than 120 degrees, in order to restrain the at least a portion of stent body 20 in the radially-compressed state.

For some applications, when restraining member 30 is in the second rotational state, such as shown in FIGS. 1D and 2C, arcuate sections 34 circumferentially overlap one another to a greater extent than when in the first rotational state, such as shown in FIGS. 1A, 1B, and 1D. For example, when restraining member 30 is in the second rotational state, arcuate sections 34 may be arranged to have maximal overlap with one another, as shown in FIG. 1D.

For some applications, when restraining member 30 is in the first rotational state, arcuate sections 34 collectively circumscribe (i.e., without double-counting the arcs of any circumferentially-overlapping portions) a complete circle, i.e., exactly one 360-degree arc, as shown in FIGS. 1A, 1B, and 1C. Alternatively, when restraining member 30 is in the first rotational state, arcuate sections 34 collectively circumscribe one or more arcs having an angular sum of at least 220 degrees (the configuration in which the sum is less than 360 degrees is not shown).

For some applications, when restraining member 30 is in the second rotational state, such as shown in FIGS. 1D and 2C, arcuate sections 34 collectively circumscribe (i.e., without double-counting the arcs of any circumferentially-overlapping portions) one or more arcs having an angular sum of no more than 150 degrees, as is approximately shown in FIG. 1D, e.g., no more than 90 degrees.

Reference is still made to FIG. 1B. For some applications, arcuate sections 34 are shaped so as to define (a) respective longitudinal base strips 42, and (b) respective pluralities of circumferential tabs 44 that extend circumferentially from respective longitudinal base strips 42. For some applications, as shown in FIG. 1B, a first subset of circumferential tabs 44 extend circumferentially clockwise from each of longitudinal base strips 42, and a second subset of circumferential tabs 44 extend circumferentially counterclockwise from the longitudinal base strip. When restraining member 30 is in the first rotational state, longitudinal base strips 42 of circumferentially-adjacent ones of arcuate sections 34 do not overlap one another, and circumferential tabs 44 overlap longitudinal base strips 42 of circumferentially-adjacent ones of arcuate sections 34. For example, as shown in FIG. 1B, the circumferential tabs 44A that extend circumferentially counterclockwise (as viewed from the top of the figure) from longitudinal base strip 42A of arcuate section 34A circumferentially overlap longitudinal base strip 42C of circumferentially-adjacent arcuate section 34C, and longitudinal base strips 42A and 42C of circumferentially-adjacent arcuate sections 34A and 34C do not circumferentially overlap one another.

Typically, longitudinal base strips 42 extend along an entire axial length of their respective arcuate sections 34, as shown in FIG. 1B. For some applications, at least one of arcuate sections 34 is shaped such that longitudinal base strip 42 thereof extends axially beyond the end-most circumferential tab(s) 44 thereof, such as shown in FIG. 1B for arcuate sections 34A and 34B (but not arcuate section 34C).

For some applications, when restraining member 30 is the second rotational state, longitudinal base strips 42 of at least some of (e.g., all of) arcuate sections 34 at least partially overlap one another.

For some applications, portions of arcuate sections 34 that restrain the at least a portion of stent body 20 in the radially-compressed state have respective lengths along the axis 40, and an average of the lengths is at least 30% of an average length of the at least a portion of stent body 20 when in the radially-compressed state. For some applications, a portion of restraining element 30 that restrains the at least a portion of stent body 20 in the radially-compressed state has a length along the axis of at least 30% of an average length of the at least a portion of stent body 20 when in the radially-compressed state.

For some applications, structural stent elements 32 comprise a shape memory alloy. For example, the shape memory alloy may comprise a nickel and titanium, and, optionally, additionally cobalt. The shape memory element may comprise any shape memory alloy known in the art that is characterized by a stress-induced martensitic state and an unstressed austenitic state. For some applications, suitable alloys are those that display stress-induced martensite at temperatures near mammalian (e.g., human) body temperature (35-40 degrees C.). For example, one such alloy is the nickel/titanium/vanadium alloy described in U.S. Pat. No. 4,505,767 to Quin, which is incorporated herein by reference. The shape memory alloy is typically configured such that stent body 20 is self-expanding when not radially restrained.

For some applications, the shape memory alloy comprises a pseudoelastic shape-memory alloy, the alloy displaying reversible stress-induced martensite at between 35 and 40 degrees C. such that it has a stress-induced martensitic state and an austenitic state. When the alloy is in the stress-induced martensitic state, stent body 20 has a deformed shape that provides the radially-compressed state. When the alloy is in the austenitic state, the stent body has a different unstressed shape that provides the radially-expanded state.

For some applications, when restraining member 30 is in the first rotational state and the shape memory alloy is at a temperature greater than an austenite start temperature of the shape memory alloy, restraining member 30 confines and stresses the memory alloy element so that the at least a portion of stent body 20 is retained in a stress-induced martensite state.

For some applications, when the at least a portion of stent body 20 is released and transitions to the radially-expanded state, the transformation of stent body 20 occurs with a change in the temperature of at least one element from the group consisting of: restraining member 30 (typically, arcuate sections 34 thereof), structural stent elements 32 comprising the shape memory alloy, and the mammalian body.

For some applications, medical apparatus 10 further comprises a heat dissipation element in thermal contact with at least one element selected from the group consisting of: restraining member 30 and structural stent elements 32. The heat dissipation element dissipates at least a portion of any heat that may be released by the stent body as it radially expands.

Figure 2B:
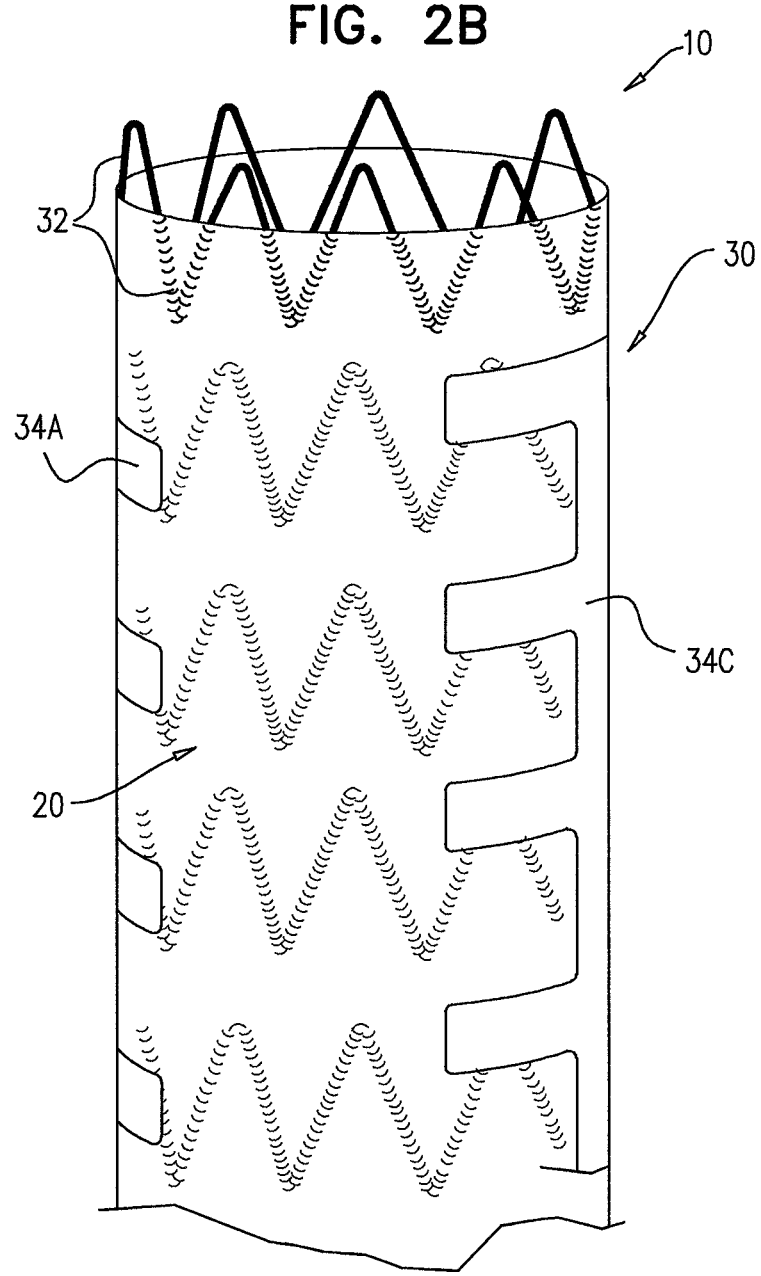

Reference is made again to FIG. 1A, and additionally to FIGS. 2A-C, which are schematic illustrations of medical apparatus 10 in several respective rotational states, in accordance with an application of the present invention. FIGS. 1A, 2A, 2B, and 2C show restraining member 30 in successively more open, i.e., less restraining, rotational states. As described above, FIG. 1A shows restraining member 30 in a first rotational state, in which restraining member 30 restrains the at least a portion of stent body 20 in the radially-compressed state. For some applications, this rotational state is the rotational state in which restraining member 30 is initially disposed, and may, for example, be delivered to a surgeon in this state. FIGS. 2A and 2B show restraining member 30 in a subsequent, different first rotational states that are successively less restraining, as arcuate members 34 are rotated toward one another into a more circumferentially dense disposition.

FIG. 2C shows restraining member 30 in the second rotational state, releasing the at least a portion of stent body 20. The stent body, as it is released, transitions to the radially-expanded state, because of the memory properties of the shape memory alloy, as discussed above.

The rotational state of restraining member 30 is typically controlled using a handle located external to the patient's body. Typically, the surgeon manually actuates (e.g., by rotating a handle, pressing on a knob, advancing a lever, etc.) one or more knobs that transmit the rotation to the arcuate sections, such as via one or more wires, shafts, and/or another gearing mechanism. Alternatively, the handle comprises one or more motors that are actuated to rotate the arcuate sections.

Figure 3A:
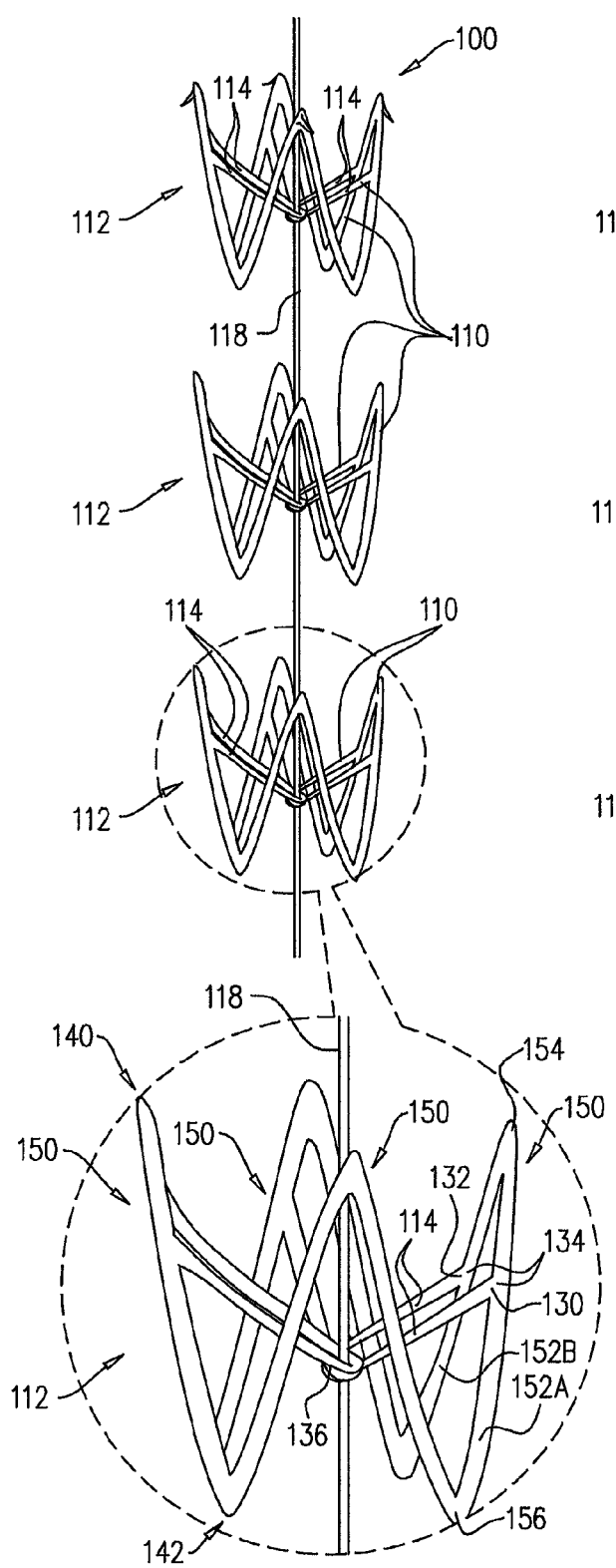
FIGS. 3A and 3B are schematic illustrations of another medical apparatus, in accordance with respective applications of the present invention.
Figure 3B:
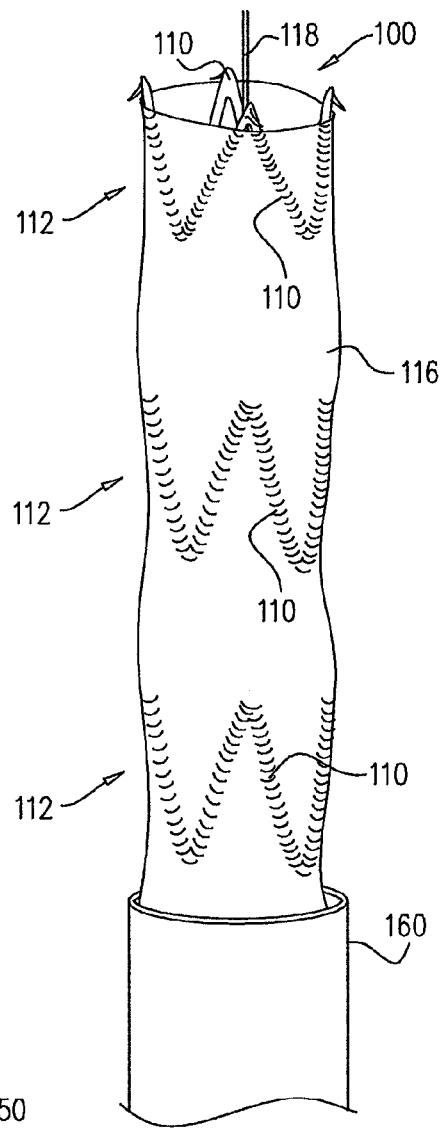

Reference is now made to FIGS. 3A and 3B, which are schematic illustrations of medical apparatus 100, in accordance with respective applications of the present invention. Medical apparatus 100 is configured for insertion into a mammalian body, such as a human body. Medical apparatus 100 comprises structural stent elements 110, at least a portion of which are shaped so as to define (a) one or more generally circumferential bands 112, such as a plurality of generally circumferential bands 112, and (b) a plurality of engagement members 114 that are joined to and extend radially inwardly from each of bands 112.

For some applications, structural stent elements 110, including the at least a portion that defines the one or more bands 112, are shaped so as to define a generally tubular structure. For some applications, as shown in FIG. 3B, medical apparatus 100 further comprises an implantable-grade fabric 116 securely attached to and at least partially covering the generally tubular structure (an inner and/or an outer surface of the structure). Fabric 116 may have the properties of fabric 34, described hereinabove with reference to FIG. 1A.

Medical apparatus 100 further comprises an elongated latch member 118 which is threaded through engagement members 114, thereby physically latching engagement members 114. Typically, elongated latch member 118 comprises a wire (typically comprising a metal, such as a metal alloy, e.g., any of the alloys described herein) or a hollow tube (which may comprise a metal, such as a metal alloy, e.g., any of the alloys described herein, or plastic).

Engagement members 114 and each of one or more bands 112 are configured such that:
 when latch member 118 is threaded through and thus physically latches engagement members 114, engagement members 114 retain the band in a radially-compressed state, as shown in FIGS. 3A and 3B; and
 when latch member 118 is removed from engagement members 114, the band assumes a radially-expanded state, as described hereinbelow with reference to FIG. 4.

Reference is still made to FIG. 3A. For some applications, engagement members 114 have (a) respective first ends 130, which are joined to and extend from one of one or more bands 112, (b) respective second ends 132, which are joined to and extend from the band at respective junctions 134, and (c) respective curved portions 136 between respective first and respective second ends 130 and 132. When latch member 118 is threaded through engagement members 114, curved portions 136 pass around latch member 118. As a result, latch member 118 holds the curved portions near a central longitudinal axis of band 112. The engagement members thus prevent the band from expanding radially.

For some applications, each of the one or more bands 118 has distal and proximal ends 140 and 142. All of engagement members 114 of a given circumferential band are shaped such that curved portions 136 thereof are disposed more proximally than junctions 134, when latch member 118 physically latches the engagement members. In other words, all of these curved portions generally extend in the same, proximal direction.

For some applications, at least a portion of the structural stent elements of each of one or more bands 112 are arranged as a plurality of pairs 150 of two respective generally straight, adjacently disposed structural stent elements 152A and 152B joined by respective peaks 154.

First end 130 of each of engagement members 114 is joined to and extends from one of the generally straight structural stent elements 152A of one of pairs 150. Second end 132 of the engagement member is joined to and extends from the other 152B of the generally straight structural stent elements of the one of pairs 150. Typically, latch member 118, when physically latching engagement members 114, rests against an inner surface of curved portion 136 of each of engagement member 114. Optionally, circumferentially-adjacent pairs 150 are connected by secondary peaks 156 at an end of the band opposite to the end at which peaks 154 are disposed.

For some applications, as shown in FIG. 3B, medical apparatus 100 further comprises a hollow, elongated delivery shaft 160, in which one or more bands 112 are initially positioned, retained by latch member 118 in the radially-compressed state. For some applications, delivery shaft 160 and one or more bands 112 are configured such that the bands, when retained by latch member 118 in the radially-compressed state, are slidably positioned in the delivery shaft. (In contrast, conventional self-expanding stents apply a radially-outwardly-directed force against the inner wall of the delivery shaft, such that such conventional stents slide in the delivery shaft while applying significant frictional force.) In this configuration of the present invention, a rapid exchange technique can be performed in which the delivery shaft can be advanced to a target site in a body lumen (typically a blood vessel), and thereafter bands 112 (typically as part of a medical device, such as a stent-graft) are advanced through the delivery shaft. Because latch member 118 holds the bands in a radially-compressed state, the bands do not apply outward force again the inner wall of the delivery shaft, and thus the bands can slide through the delivery shaft. After the desired site is reached, the delivery shaft is withdrawn, leaving the bands in place. The bands are then allowed to radially expand by removal of the latch member 118, as described herein.

Alternatively, for some applications, delivery shaft 160 and one or more bands 112 are configured such that the shaft snugly (non-slidably) holds the bands in a second radially-compressed state that is more radially compressed than the radially-compressed state in which latch member 118 restrains the bands. Proximal withdrawal of the delivery shaft with respect to the bands releases the bands to a partial deployment state, in which the bands are in the radially-compressed state in which latch member 118 restrains the bands. When the latch member is removed from the engagement members, the bands assume the radially-expanded state, thereby completing deployment. This two-stage deployment approach may be useful in cases where deployment accuracy—axial and/or orientational—is of high importance, such as when deploying a main stent-graft module that has side-branch fenestrations, which fenestrations should be positioned as accurately as possible relative to the anatomical side branches.

For some applications, structural stent elements 110 comprise a shape memory alloy. For example, the shape memory alloy may comprise a nickel and titanium, and, optionally, additionally cobalt. The shape memory element may comprise any shape memory alloy known in the art that is characterized by a stress-induced martensitic state and an unstressed austenitic state. For some applications, suitable alloys are those that display stress-induced martensite at temperatures near mammalian (e.g., human) body temperature (35-40 degrees C.). For example, one such alloy is the nickel/titanium/vanadium alloy described in U.S. Pat. No. 4,505,767 to Quin, which is incorporated herein by reference. The shape memory alloy is typically configured such that bands 112 are self-expanding when not radially restrained.

For some applications, the shape memory alloy comprises a pseudoelastic shape-memory alloy, the alloy displaying reversible stress-induced martensite at between 35 and 40 degrees C. such that it has a stress-induced martensitic state and an austenitic state. When the alloy is in the stress-induced martensitic state, each of one or more bands 112 has a deformed shape that provides the radially-compressed state. When the alloy is in the austenitic state, each of the bands has a different unstressed shape that provides the radially-expanded state.

For some applications, one or more bands 112 and engagement members 114 are configured such that:
   when latch member 118 physically latches engagement members 114 and the shape memory alloy is at a temperature greater than an austenite start temperature of the shape memory alloy, the latch member retains the shape memory alloy of the one or more bands so that at least a portion of the alloy is in at least a partially stress-induced martensitic state and the one or more bands are in the deformed shape, and
   when latch member 118 is removed from the plurality of engagement members 114 and the shape memory alloy is at a temperature greater than the austenite start temperature, at least a portion of the shape memory alloy at least partially transitions to an austenitic state from the stress-induced martensitic state, thereby causing a transformation of the one or more bands from the deformed shape to the unstressed shape.

For some applications, the shape memory alloy is realized such that the transformation occurs without any change in temperature of the latch member or the shape memory alloy. Alternatively, the shape memory alloy is realized such that the transformation occurs with a change in temperature of at least one element selected from group consisting of: the latch member and the shape memory alloy.

For some applications, latch member 118 is configured to function as a heat dissipation element, which is in physical contact with the shape memory alloy at least when the latch member physically latches engagement members 114. For some applications, latch member 118, when physically latching engagement members 114, is disposed adjacent to at least a portion of the shape memory alloy. Alternatively or additionally, for some applications, latch member 118, when physically latching engagement members 114, is in direct physical contact with at least a portion of the shape memory alloy. The latch member, functioning as the heat dissipation element, dissipates at least a portion of any heat that may be released by bands 112 as they radially expand.

For some applications, latch member 118 is configured to function as a heat application element, which is in thermal contact with the shape memory alloy at least when the latch member physically latches engagement members 114. For some applications, latch member 118, when physically latching engagement members 114, is disposed adjacent to at least a portion of the shape memory alloy. Alternatively or additionally, for some applications, latch member 118, when physically latching engagement members 114, is in direct physical contact with at least a portion of the shape memory alloy. The latch member, functioning as the heat application element, applies at least a portion of any heat that may be absorbed by bands 112 as they radially expand.

For some applications, medical apparatus 100 further comprises a heat dissipation element, which is in thermal contact with the shape memory alloy at least when one or more bands 112 are in the radially-compressed state. For some applications in which elongated delivery shaft 160 is provided, the elongated delivery shaft comprises the heat dissipation element. The heat dissipation element dissipates at least a portion of any heat that may be released by bands 112 as they radially expand.

For some applications, the heat dissipation element is disposed adjacent to at least part of the shape memory alloy while the shape memory alloy is in the stress-induced martensitic state.

For some applications, the heat dissipation element comprises a plurality of heat dissipation elements. For some applications, the heat dissipation element is adapted to lose thermal energy at a rate faster than the rate of change of thermal energy caused by the change in temperature.

For some applications, medical apparatus 100 further comprises a heat application element, which is in thermal contact with the shape memory alloy at least when one or more bands 112 are in the radially-compressed state. For some applications in which elongated delivery shaft 160 is provided, the elongated delivery shaft comprises the heat dissipation element. The heat application element applies at least a portion of any heat that may be absorbed by bands 112 as they radially expand.

For some applications, the heat application element is disposed adjacent to at least part of the shape memory alloy while the shape memory alloy is in the stress-induced martensitic state.

For some applications, the heat application element comprises a plurality of heat application elements.

Figure 4:
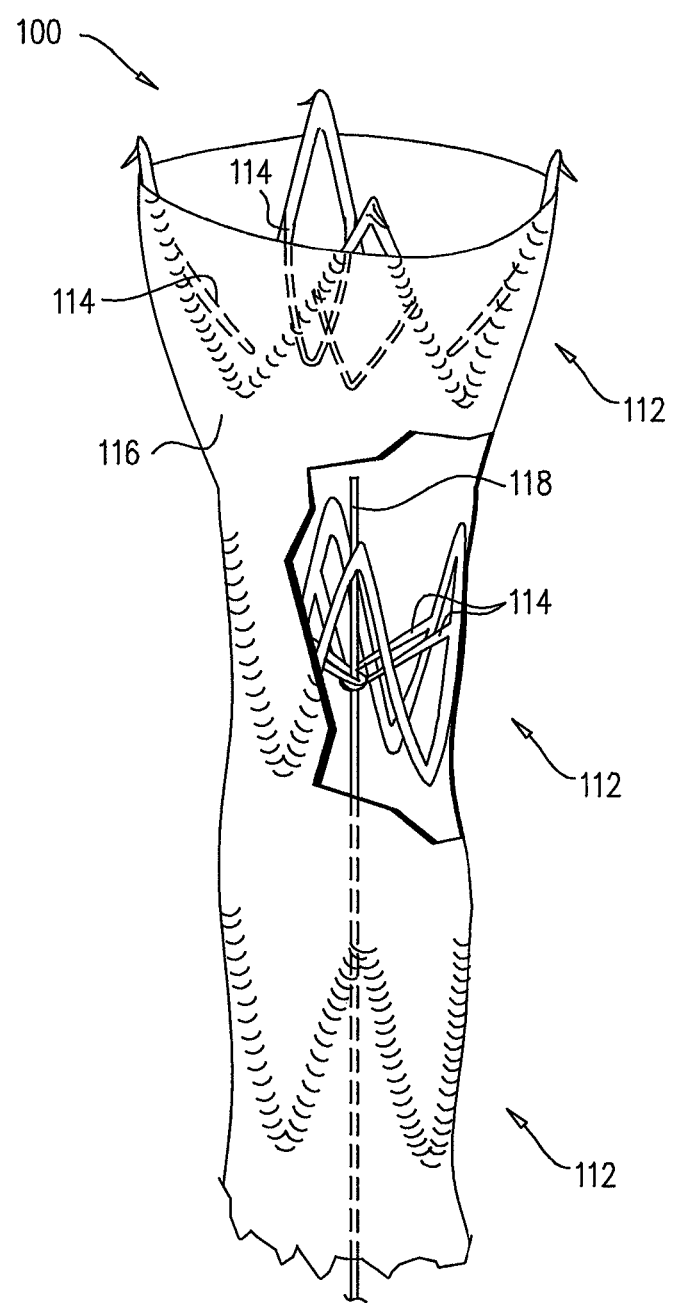
FIG. 4 is a schematic illustration of the medical apparatus of FIGS. 3A and 3B in a partially radially-expanded state, in accordance with an application of the present invention.

Reference is made to FIG. 4, which is a schematic illustration of medical apparatus 100 in a partially radially-expanded state, in accordance with an application of the present invention. In this configuration, medical apparatus 100 comprises fabric 116, as described hereinabove with reference to FIG. 3B, and a plurality of bands 112. Latch member 118 has been partially withdrawn. In particular, latch member 118 has been withdrawn from engagement members 114 of the uppermost band 112 in the figure, but is still threaded through and physically latching engagement members 114 of the middle and lowermost bands 112. As a result, uppermost band 112 has assumed the radially-expanded state, while middle and lowermost bands 112 are still restrained by latch member 118 in the radially-compressed state.

Reference is now made to FIGS. 5A and 5B, which are schematic illustrations of medical apparatus 200, in accordance with respective applications of the present invention. Medical apparatus 200 is configured for insertion into a mammalian body, such as a human body. Medical apparatus 200 is similar in some respects to medical apparatus 100, described hereinabove with reference to FIGS. 3A-4, and may implement any of the configurations in the applications described hereinabove for medical apparatus 100. Medical apparatus comprises structural stent elements 210, at least a portion of which are shaped so as to define (a) one or more generally circumferential bands 212, such as a plurality of generally circumferential bands 112, and (b) a plurality of engagement members 214 that are joined to and extend radially inwardly from each of bands 212.

For some applications, structural stent elements 210, including the at least a portion that defines the one or more bands 212, are shaped so as to define a generally tubular structure. For some applications, as shown in FIG. 5B, medical apparatus 200 further comprises an implantable-grade fabric 216 securely attached to and at least partially covering the generally tubular structure (an inner and/or an outer surface of the structure). Fabric 216 may have the properties of fabric 34, described hereinabove with reference to FIG. 1A.

Medical apparatus 200 further comprises an elongated latch member 218 which is threaded through engagement members 214, thereby physically latching engagement members 214. Typically, elongated latch member 218 comprises a wire or a hollow tube.

Engagement members 214 and each of one or more bands 212 are configured such that:
  when latch member 218 is threaded through and thus physically latches engagement members 214, engagement members 214 retain the band in a radially-compressed state, as shown in FIG. 5A, and for the lower two bands 218 shown in FIG. 5B; and
  when latch member 218 is removed from engagement members 214, the band assumes a radially-expanded state, as shown in the uppermost band 218 shown in FIG. 5B.

Reference is still made to FIG. 5A. For some applications, engagement members 214 have (a) respective first ends 230, which are joined to and extend from one of one or more bands 212, (b) respective second ends 232, which are joined to and extend from the band at respective junctions 234, and (c) respective curved portions 236 between respective first and respective second ends 230 and 232. When latch member 218 is threaded through engagement members 214, curved portions 236 pass around latch member 218. As a result, latch member 218 holds the curved portions near a central longitudinal axis of band 212. The engagement members thus prevent the band from expanding radially.

For some applications, each of the one or more bands 218 has distal and proximal ends 240 and 242. A first subset 244 of engagement members 214 are shaped such that curved portions 236 thereof are disposed more distally than junctions 234 thereof, and a second subset 246 of engagement members 214 are shaped such that curved portions 236 thereof are disposed more proximally than junctions 234 thereof. In other words, the curved portions of first subset 244 generally extend in the opposite direction as the curved portions of second subset 246. First and second subsets 244 and 246 do not include any common engagement members 214, i.e., are non-overlapping sets. This configuration may prevent engagement members 214 from giving band 218 a biased shape.

For some applications, structural stent elements 210 comprise a shape memory alloy, such as described regarding structural stent elements 110 hereinabove with reference to FIGS. 3A-4.

Reference is still made to FIG. 5B, which shows medical apparatus 200 in a partially radially-expanded state. Latch member 218 has been partially withdrawn. In particular, latch member 218 has been withdrawn from engagement members 214 of the uppermost band 212 in the figure, but is still threaded through and physically latching engagement members 214 of the middle and lowermost bands 212. As a result, uppermost band 212 has assumed the radially-expanded state, while middle and lowermost bands 212 are still restrained by latch member 218 in the radially-compressed state.

Although the techniques described herein have been generally described for implanting a stent-graft in a blood vessel, the techniques maybe used to implant other implantable medical devices that are introduced into the body in a relatively compact state and used within the body in a relatively expanded state. Non-limiting examples of such implantable medical devices include stents, coil stents and filters, catheters, cannulas, intrauterine contraceptive devices (IUDs), bone plates, marrow nails, dental arch wires, filters, bone staples, heart valves, and clips.

The scope of the present invention includes embodiments described in the following applications, which are assigned to the assignee of the present application and are incorporated herein by reference. In an embodiment, techniques and apparatus described in one or more of the following patent applications are combined with techniques and apparatus described herein. In particular, the techniques with reference to FIGS. 1-2C, the techniques described herein with reference to FIGS. 3A-4, and the techniques described herein with reference to FIGS. 5A-B, may be used to deliver any of the radially-compressible stent-grafts and stents described in the following patent applications.

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.
U.S. Provisional Application 60/892,885, filed Mar. 5, 2007
U.S. Provisional Application 60/991,726, filed Dec. 2, 2007
PCT Application PCT/IL2008/001621, filed Dec. 15, 2008, which published as PCT Publication WO 2009/078010
U.S. Provisional Application 61/219,758, filed Jun. 23, 2009
U.S. Provisional Application 61/221,074, filed Jun. 28, 2009
PCT Application PCT/IB2010/052861, filed Jun. 23, 2010, which published as PCT Publication WO 2010/150208
PCT Application PCT/IL2010/000549, filed Jul. 8, 2010, which published as PCT Publication WO 2011/004374
PCT Application PCT/IL2010/000564, filed Jul. 14, 2010, which published as PCT Publication WO 2011/007354
PCT Application PCT/IL2010/000917, filed Nov. 4, 2010, which published as PCT Publication WO 2011/055364
PCT Application PCT/IL2010/000999, filed Nov. 30, 2010, which published as PCT Publication WO 2011/064782
PCT Application PCT/IL2010/001018, filed Dec. 2, 2010, which published as PCT Publication WO 2011/067764
PCT Application PCT/IL2010/001037, filed Dec. 8, 2010, which published as PCT Publication WO 2011/070576
PCT Application PCT/IL2011/000135, filed Feb. 8, 2011, which published as PCT Publication WO 2011/095979
U.S. application Ser. No. 13/031,871, filed Feb. 22, 2011, which published as US Patent Application Publication 2011/0208289

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   providing (a) structural stent elements, at least a portion of which are shaped so as to define (i) a generally circumferential band, and (ii) a plurality of engagement members that (x) are joined to and extend radially inwardly from the band, and (y) have respective curved portions, wherein the curved portion of each of the engagement members joins respective ends of two stent element portions of the engagement member, and (b) an elongated latch member which is threaded through the engagement members, thereby physically latching the engagement members;
   transvascularly introducing the band into a blood vessel of a mammalian subject while the band is positioned in a hollow, elongated delivery shaft, with the latch member threaded through and thus physically latching the engagement members, such that the curved portions pass around the latch member, the latch member holds the curved portions radially centered within the band at a central longitudinal axis of the band, and the engagement members retain the band in a radially-compressed state; and
   thereafter, transitioning the band to a radially-expanded state by removing the latch member from the engagement members,
   wherein transvascularly introducing comprises advancing the delivery shaft to a target site in the blood vessel, and thereafter sliding the band through at least a portion of the delivery shaft while the band is retained by the latch member in the radially-compressed state.

2. The method according to claim 1, wherein providing the latch member comprises providing a latch member that includes an element selected from the group consisting of: a wire and a hollow tube.

3. The method according to claim 1,
   wherein the structural stent elements, including the at least a portion that defines the band, are shaped so as to define a generally tubular structure, and
   further comprising providing a main stent-graft that includes the structural stent elements and an implantable-grade fabric securely attached to and at least partially covering the generally tubular structure, wherein the main stent-graft module has side-branch fenestrations, and
   wherein the method further comprises positioning the fenestrations relative to anatomical side branches of the blood vessel.

4. The method according to claim 1, wherein providing the structural stent elements comprises providing structural stent elements that comprise a shape memory alloy.

5. The method according to claim 1, wherein the generally circumferential band includes a plurality of generally circumferential bands, and wherein respective sets of the plurality of engagement members are joined to respective ones of the bands.

* * * * *